(12) United States Patent
Freeman

(10) Patent No.: US 6,726,634 B2
(45) Date of Patent: Apr. 27, 2004

(54) SYSTEM AND METHOD FOR DETERMINING A CONDITION OF A PATIENT

(75) Inventor: Curtis W. Freeman, Windham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/056,364

(22) Filed: Jan. 25, 2002

(65) Prior Publication Data

US 2003/0144699 A1 Jul. 31, 2003

(51) Int. Cl.[7] .............................................. A61B 5/0402
(52) U.S. Cl. .............................. 600/508; 600/513; 607/4
(58) Field of Search ................................ 600/510, 508, 600/509, 513; 607/4, 5, 9, 10, 6

(56) References Cited

U.S. PATENT DOCUMENTS

| 5,438,983 | A |  | 8/1995 | Falcone | 128/630 |
| 5,697,955 | A | * | 12/1997 | Stolte | 607/6 |
| 5,957,856 | A |  | 9/1999 | Weil et al. | 600/518 |
| 6,047,212 | A |  | 4/2000 | Gliner et al. | 607/7 |
| 6,171,257 | B1 | * | 1/2001 | Weil et al. | 600/518 |
| 6,304,773 | B1 | * | 10/2001 | Taylor et al. | 600/515 |
| 6,440,082 | B1 | * | 8/2002 | Joo et al. | 607/6 |
| 2002/0193848 | A1 |  | 12/2002 | Lyster et al. | 607/62 |

FOREIGN PATENT DOCUMENTS

| WO | WO9724062 | 10/1997 | ......... A61B/8/0452 |

* cited by examiner

*Primary Examiner*—George R. Evanisko
(74) *Attorney, Agent, or Firm*—Tony Piotrowski

(57) ABSTRACT

A system and method for determining whether further efforts to resuscitate will be unsuccessful, is provided. One embodiment of the system comprises a memory that comprises a memory module. The memory module comprises a program that analyzes digital data that corresponds to a first parameter to determine whether the first parameter is valid; determines whether the first parameter is in a first futile range; and analyzes the first parameter to determine whether further efforts to resuscitate will be unsuccessful.

25 Claims, 8 Drawing Sheets

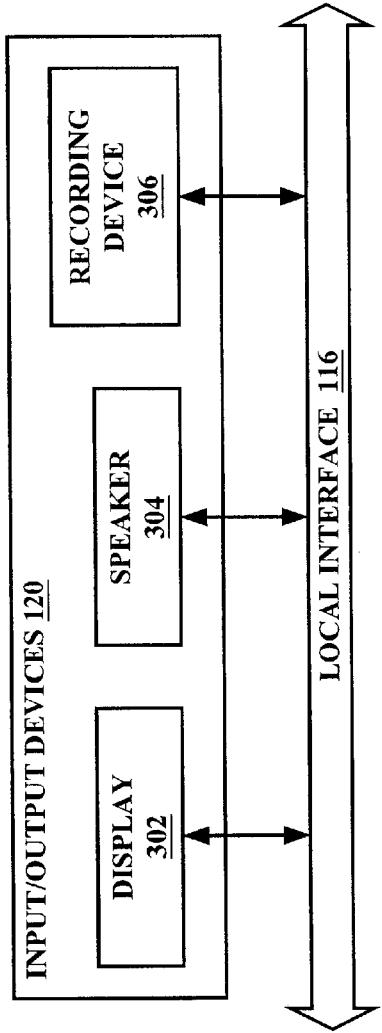

SYSTEM AND METHOD FOR DETERMINING A CONDITION OF A PATIENT

CROSS-REFERENCE TO RELATED APPLICATION

This application is related to co-pending U.S. utility patent application entitled "External Defibrillator Instruction System and Method" filed on Jun. 23, 2000, and accorded Ser. No. 09/603,270, which is entirely incorporated herein by reference.

TECHNICAL FIELD

The present invention is generally related to biotechnology, and, more particularly, is related to a system and method for determining whether further efforts to resuscitate will be unsuccessful.

BACKGROUND OF THE INVENTION

When a patient is subjected to trauma such as ventricular fibrillation, cardiac arrest, heart attack, or ventricular tachycardia, resuscitation can be used to alleviate the trauma and help the patient to survive. The patient can be an individual, or an animal. Resuscitation includes, but is not limited to, cardiopulmonary resuscitation (CPR), and defibrillation.

During the resuscitation effort, however, a rescuer, such as a paramedic, a doctor, a nurse, a medical personnel, or any person rescuing the patient, generally, does not know if his/her efforts to resuscitate the patient will be unsuccessful. In other words, the rescuer cannot predict whether resuscitation will enable the patient to survive. While attempting to resuscitate the patient, the rescuer continually monitors the patient to determine whether the patient is responding to the resuscitation effort, and the end result can be that the patient dies despite the resuscitation effort.

Hence, a need exists in the industry to overcome the above-mentioned problem of the rescuer continually monitoring the patient to determine whether the patient is responding to the resuscitation effort, and/or other inadequacies and/or deficiencies.

SUMMARY OF THE INVENTION

The present invention provides a system and method for determining whether further efforts to resuscitate will be unsuccessful.

Briefly described, in architecture, one embodiment of the system, among others, comprises a memory comprising a memory module, the memory module comprising a program that analyzes digital data that corresponds to a first parameter to determine whether the first parameter is valid; determines whether the first parameter is in a first futile range; and analyzes the first parameter to determine whether further efforts to resuscitate will be unsuccessful.

The present invention can also be viewed as providing a method for determining whether further efforts to resuscitate will be unsuccessful. In this regard, one embodiment of such a method, among others, can be broadly summarized by the following steps: analyzing digital data that corresponds to a first parameter to determine whether the first parameter is valid; determining whether the first parameter is in a first futile range; and analyzing the first parameter to determine whether further efforts to resuscitate will be unsuccessful.

Other features and advantages of the present invention will be or become apparent to one with skill in the art upon examination of the following drawings and detailed description. It is intended that all such additional features and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 3 is a block diagram of an example of input/output devices that the monitoring device of FIGS. 1 and 2, include.

FIG. 4 is a block diagram of an example of a power source that provides power to the monitoring device of FIGS. 1 and 2.

DETAILED DESCRIPTION OF THE PREFERRED EMBODIMENT

Figure 1:
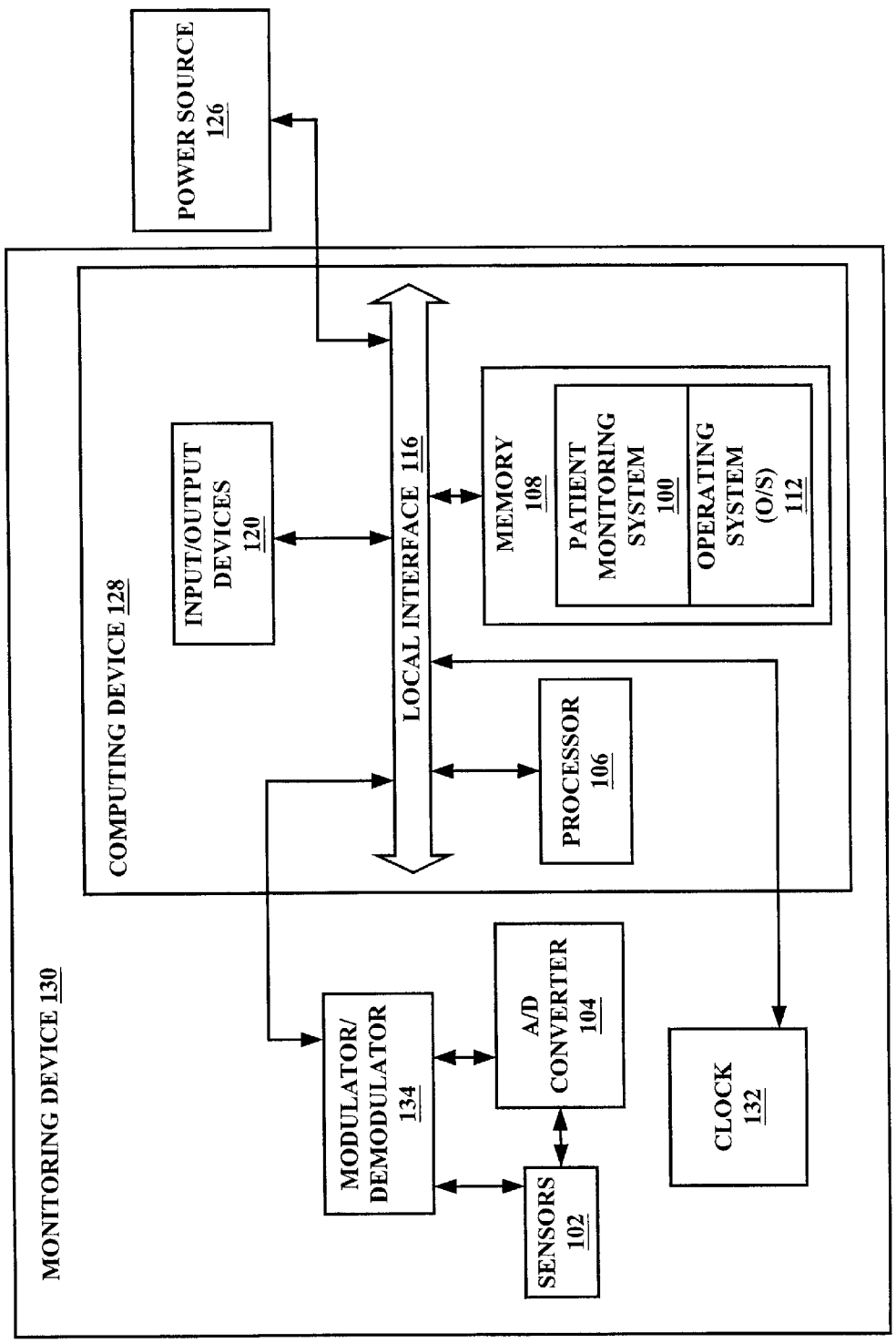
FIG. 1 is a block diagram illustrating an embodiment of a monitoring device that includes a patient monitoring system, which is the system for determining whether further efforts to resuscitate will be unsuccessful.

FIG. 1 is a block diagram illustrating an embodiment of a monitoring device 130 that includes a patient monitoring system 100. The monitoring device 130 could be, for instance, an electrocardiogram machine. The monitoring device 130 also includes sensors 102, an analog-to-digital (A/D) converter 104, a computing device 128, a clock 132, and a modulator/demodulator 134. The computing device 128 includes a processor 106, a memory 108, a local interface 116, and input/output (I/O) devices 120. The memory 108 includes the patient monitoring system 100, and an operating system (O/S) 112.

The local interface 116 can be, for example, but not limited to, one or more buses or other wired or wireless connections. The local interface 116 may have additional elements, which are omitted for simplicity, such as controllers, buffers, drivers, repeaters, and receivers to enable communications. Further, the local interface 116 may include address, control, and/or data connections to enable appropriate communications among the aforementioned components.

The processor 106 is a hardware device for executing software, particularly that is stored in memory 108. The processor 106 can be any custom made or commercially available processor, a central processing unit (CPU), an auxiliary processor among several processors associated with the computing device 128, a semiconductor based microprocessor in the form of a microchip or chip set, a macroprocessor, or generally any device for executing software instructions. Examples of commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc, or a 68xxx series microprocessor from Motorola Corporation.

The memory 108 can include any one or combination of volatile memory elements such as random access memory (RAM) and nonvolatile memory elements such as read-only memory (ROM), hard drive, tape, and Compact Disc ROM (CDROM). Different types of RAM are dynamic RAM (DRAM), static RAM (SRAM), and synchronous DRAM (SDRAM). Moreover, the memory 108 may incorporate electronic, magnetic, optical, and/or other types of storage media. Note that the memory 108 can have a distributed architecture, where various components are situated remote from one another, but can be accessed by the processor 106.

The software in the memory 108 may include one or more separate programs, each of which includes an ordered listing of executable instructions for implementing logical functions. In the example of FIG. 1, the software in the memory 108 includes the patient monitoring system 100 and the operating system (O/S) 112. A nonexhaustive list of examples of commercially available operating systems is an Operating System Embedded (OSE) from Enea Systems Inc.; a Windows O/S available from Microsoft Corporation; a Netware O/S available from Novell, Inc.; a Macintosh O/S available from Apple Computing device, Inc.; a NetWare O/S available from Novell, Inc.; a UNIX O/S, which is available for purchase from many vendors, such as the Hewlett-Packard Company, Sun Microsystems, Inc., and AT&T Corporation; a LINUX O/S, which is freeware that is readily available on the Internet; a run time Vxworks O/S from WindRiver Systems, Inc.; and an appliance-based O/S, such as that implemented in handheld computing devices or personal digital assistants (PDAs). Examples of PDAs include PalmOS available from Palm Computing, Inc., and Windows CE available from Microsoft Corporation. The O/S 112 essentially controls the execution of other computer programs, such as the patient monitoring system 100, and provides scheduling, input-output control, file and data management, memory management, and communication control and related services.

The patient monitoring system 100 is a source program, executable program (object code), script, or any other entity that includes a set of instructions to be performed. When implemented as a source program, the program is typically translated via a compiler, assembler, interpreter, or the like, which may or may not be included within the memory 108, so as to operate properly in connection with the O/S 112. Furthermore, the patient monitoring system 100 can be written as (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada.

The I/O devices 120 may include input devices, for example, but not limited to, a keyboard, mouse, scanner, or a microphone. Furthermore, the I/O devices 120 may also include output devices, for example but not limited to, a printer, a display, and a speaker. Finally, the I/O devices 120 may further include devices that communicate both inputs and outputs, for instance, but not limited to, the modulator/demodulator 134 for accessing another device, system, or network, a radio frequency (RF) or other transceiver, a telephonic interface, a bridge, a recording device, and a router.

If the computing device 128 is a PC, workstation, or the like, the software in the memory 108 may further include a basic input output system (BIOS) (omitted for simplicity). The BIOS is a set of essential software routines that initialize and test hardware at startup, start the O/S 112, and support the transfer of data among the hardware devices. The BIOS is stored in the ROM so that the BIOS can be executed when the computing device 128 is activated.

When the computing device 128 is in operation, the processor 106 is configured to execute software stored within the memory 108, to communicate data to and from the memory 108, and to generally control operations of the computing device 128 pursuant to the software. The patient monitoring system 100 and the O/S 112, in whole or in part, but typically the latter, are read by the processor 106, perhaps buffered within the processor 106, and then executed.

The sensors 102 may include, for example, pads or paddles that are attached to the patient to measure various physiological parameters of the patient. The various physiological parameters will be referred to as the various parameters. Alternatively, the sensors 102 can include an endotracheal tube that is inserted into the trachea of the patient. Alternatively, the sensors 102 can include a cannula that measures the invasive blood pressure of the patient, a percent oxygen saturation ($SpO_2$) transducer that measures percent oxygen saturation in the patient's blood, or an end tidal carbon dioxide ($EtCO_2$) sensor that measures expired $CO_2$ concentration from the patient's airway.

The local interface 116 couples the processor 106, the memory 108, the I/O devices 120, power source 126, the clock 132, and the modulator/demodulator 134. The modulator/demodulator 134 is coupled to the sensors 102 and the A/D converter 104. The sensors 102 are coupled to the A/D converter 104.

The power source 126 provides power to the sensors 102, via the local interface 116, and the modulator/demodulator 134. The power source 126 also provides power to the A/D converter 104, via the local interface 116 and the modulator/demodulator 134. Moreover, the power source 126 provides power to the computing device 128, the clock 132, and the modulator/demodulator 134. The monitoring device 130, may, alternatively, include the power source 126. When the rescuer operates the I/O devices 120, the sensors 102 measure one of the various parameters of the patient. The various parameters include, but are not limited to, end tidal carbon dioxide ($EtCO_2$) level, invasive blood pressures such as arterial blood pressure (ABP) or non-invasive blood pressure (NBP), central perfusion pressure (CPP), central venous oxygen saturation ($SvO_2$), central venous pressure (CVP), agonal rhythm, asystole, heart rate (HR), percent oxygen saturation ($SpO_2$) in the blood of the patient, and any other parameters of the patient.

In general terms, $EtCO_2$ is the partial pressure or maximal concentration of $CO_2$ at the end of an exhaled breath of the patient. The partial pressure or maximal concentration of $CO_2$ is expressed as a percentage of $CO_2$ or millimeter level of mercury (mm Hg). CPP is generally defined as the difference between mean arterial and intracranial pressures, both of which are invasive blood pressures measured at different points within the patient's body. Percent oxygen saturation is typically defined as an invasive version of central venous oxygen saturation. In general, central venous oxygen saturation is percent oxygen saturation measured by a transducer in the patient's venous system. Blood from systemic veins of the patient flows into the patient's right atrium. Generally, pressure in the right atrium is the CVP. The CVP is a function of right side of the heart of the patient, and the pressure of venous blood in the patient's vena cava. Typically, agonal rhythm is a terminal rhythm and is usually the last rhythm before asystole, where asystole is the absence of contractions of the heart of the patient.

The sensors 102 measure one of the various parameters and output an analog signal to the A/D converter 104. The A/D converter 104 converts the analog signal to a digital signal. Alternatively, the sensors 102 may directly output a digital signal to the modulator/demodulator 134 if the sensors 102 include the A/D converter 104, or are capable of generating a digital signal. The modulator/demodulator 134 extracts digital data from the digital signal. The modulator/demodulator 134 can also convert digital data into a digital signal. The modulator/demodulator 134 can perform any kind of modulation/demodulation, including but not limited to, amplitude modulation (AM), phase modulation (PM), frequency modulation (FM), pulse amplitude modulation (PAM), carrierless amplitude/phase modulation (CAP), discrete multitone modulation (DMT), discrete wavelet multitone modulation (DWMT), and quadrature amplitude modulation (QAM).

The memory 108 stores the digital data. The I/O devices 120 output one of the various parameters that correspond to the digital data. For example, a display 302 (FIG. 3) that the I/O devices 120 may include, shows a parameter of 15 mm Hg, which is an $EtCO_2$ level that corresponds to digital data 00010101. The digital data 0001 in binary translates into a 1 in decimal, and the digital data 0101 translates into a 5 in decimal, and hence, the display 302 (FIG. 3) shows 15 mm Hg. The patient monitoring system 100 receives the digital data that is output from the modulator/demodulator 134, and may command the I/O devices 120 to indicate that further efforts to resuscitate the patient will be unsuccessful.

Figure 2:
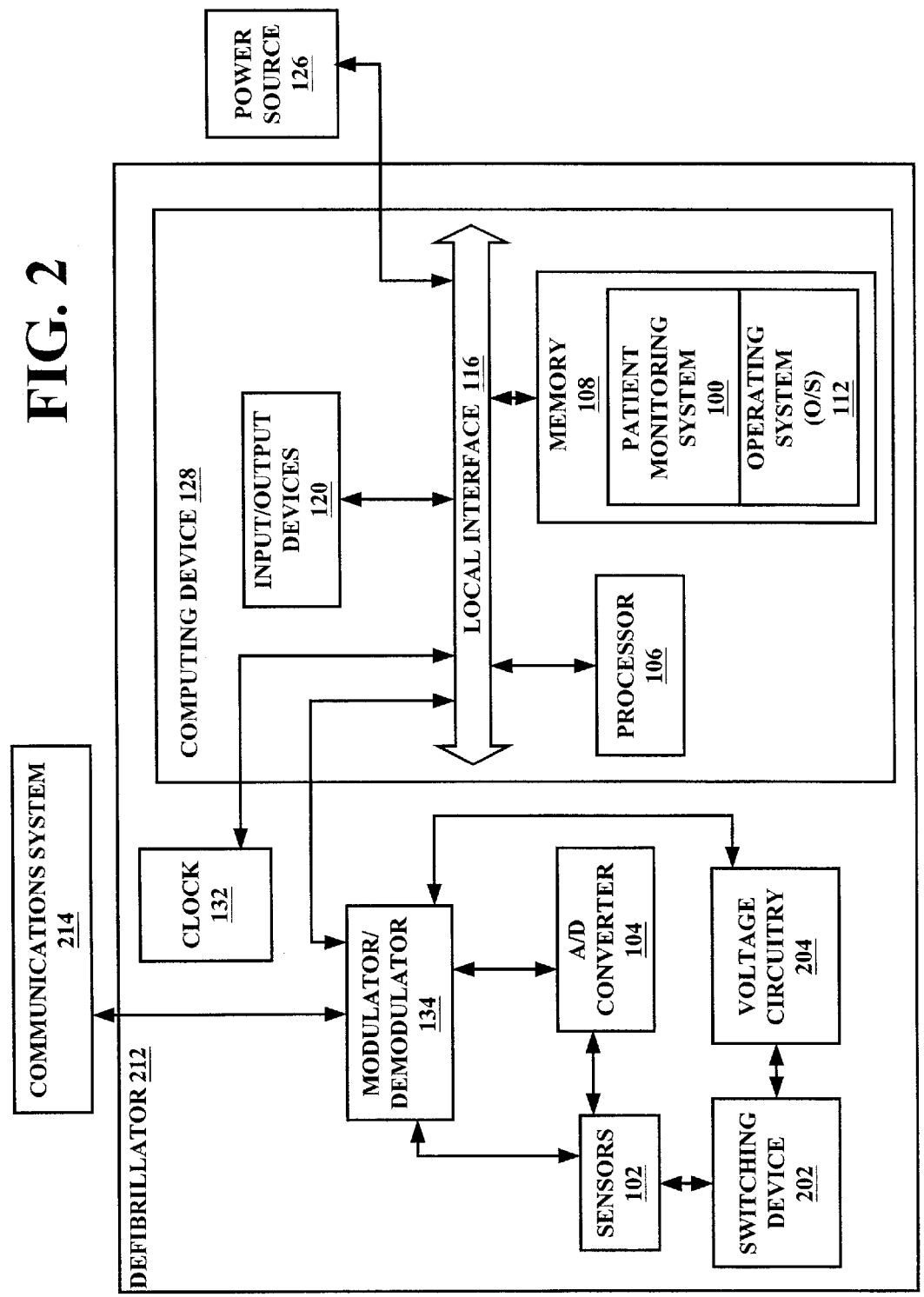
FIG. 2 is a block diagram illustrating another embodiment of the monitoring device of FIG. 1, where the embodiment includes the patient monitoring system.

FIG. 2 is a block diagram illustrating another embodiment of the monitoring device 130 of FIG. 1. This embodiment is a defibrillator 212. The defibrillator 212 includes the sensors 102 (FIG. 1), the A/D converter 104 (FIG. 1), the computing device 128 (FIG. 1), the clock 132 (FIG. 1), the modulator/demodulator 134 (FIG. 1), a switching device 202, and voltage circuitry 204. The local interface 116 couples the processor 106, the memory 108, the I/O devices 120, the power source 126 (FIG. 1), the clock 132, and the modulator/demodulator 134. The modulator/demodulator 134 is coupled to the sensors 102, the A/D converter 104, the voltage circuitry 204, and a communications system 214. The switching device 202 is coupled to the voltage circuitry 204, and the sensors 102.

The switching device 202 includes one or more switches such as metal-oxide-semiconductor-field-effect transistors (MOSFETs), relays, or any other switches. The switching device 202 also includes switching logic. The voltage circuitry 204 includes one or more capacitors, or any other devices that store charge. The communications system 214 includes, for example, an RS-232, a bluetooth, or a communications network. Examples of the communications network include, but are not limited to, integrated services digital network (ISDN), and a public service telephone network (PSTN).

The sensors 102, the A/D converter 104, the modulator/demodulator 134, and the patient monitoring system 100 perform the same functions as those performed while describing FIG. 1. The power source 126 provides power to the computing device 128, the clock 132, and the modulator/demodulator 134. The power source 126 also provides power to the sensors 102, the A/D converter 104, and the voltage circuitry 204 via, for instance, the local interface 116 and the modulator/demodulator 134. Moreover, the power source 126 provides power to the switching device 202 via, for example, the local interface 116, the modulator/demodulator 134, and the voltage circuitry 204. The power source 126, alternatively, may be located in the defibrillator 212.

The I/O devices 120 control the voltage circuitry 204. For example, the rescuer can charge the capacitor in the voltage circuitry 204, by pressing a key on a keyboard that can be one of the I/O devices 120.

The switching device 202 couples the voltage circuitry 204 to the sensors 102 based on the operation of the I/O devices 120. During defibrillation of the patient, when an individual operating the defibrillator 212 presses a button on the I/O devices 120, the actuation of the button commands the switching device 202 to connect the voltage circuitry 204 to one or more of the sensors 102. Switching logic, in the switching device 202, may only couple one or more, but not all of the sensors 102, to the voltage circuitry 204. The modulator/demodulator 134 modulates the command into a signal. The switching device 202 then establishes a connection between the sensors 102 and the voltage circuitry 204. The voltage circuitry 204 discharges the stored charge, via the sensors 102, to the patient. Alternatively, when the sensors 102 measure the various parameters of the patient, there is no such discharge, and so the switching device 202 does not connect the sensors 102 to the voltage circuitry 204.

The communications system 214 communicates signals that correspond to the digital data stored in the memory 108 stores, to other systems such as a computing device (not shown). The computing device (not shown) may be located in a central office, a hospital, a house, a place where the patient is being monitored, or any other location. For example, an ISDN propagates signals corresponding to the digital data that corresponds to the $EtCO_2$ level, to a server in a hospital. The communications system 214 receives similar signals from the computing device (not shown).

FIG. 3 is a block diagram of an example of the I/O devices 120 that may be included in the monitoring device 130 (FIG. 1), and the defibrillator 212 (FIG. 2). The I/O devices 120 include the display 302, a speaker 304, and a recording device 306. The local interface 116 (FIGS. 1 and 2) couples the display 302, the speaker 304, and the recording device 306 to each other, and to the processor 106 (FIGS. 1 and 2).

The display 302 can be, for example, a screen that displays the various parameters. The display 302 can be a screen of a monitor, a screen of a handheld PDA, or any other screen. The speaker 304 is a device that outputs voices or tones that corresponds to the various parameters.

The modulator/demodulator 134 (FIGS. 1 and 2) can be located between the local interface 116 and a digital-to-analog (D/A) converter (not shown), to convert digital data that corresponds to one of the various parameters, into a digital signal. The D/A converter (not shown) can be located between the modulator/demodulator 134 (FIGS. 1 and 2) and the speaker 304 to convert the digital signal into an analog signal. The speaker 304 then outputs voices or tones that correspond to the analog signal. Alternatively, the speaker 304 can output voices or tones that correspond to the digital signal if the digital signal is not converted to the analog signal.

The recording device 306 is a device that records, stores, and/or outputs information that is obtained from an environment surrounding the recording device 306. The recording device 306 can be a tape recorder, a microcassette recorder, a video cassette recorder, or any other recorder. For example, the recording device 306 can record a conversation between two rescuers while resuscitating the patient. The recording device 306 then stores the conversation in a memory device, and the conversation can be later played to detect the events that took place during the resuscitation effort. Alternatively, the memory 108 (FIGS. 1 and 2) can record the conversation.

FIG. 4 is a block diagram of an example of the power source 126 of FIGS. 1 and 2. The power source 126 includes a power adjuster 404, a battery 310, an alternating current (AC) source 412, and a direct current (DC) source 414. The battery 410, the AC source 412, and the DC source 414 are coupled to the power adjuster 404. The power adjuster 404 is coupled to the local interface 116 (FIGS. 1–3).

The power adjuster 404 can be implemented with any or a combination of the following technologies: a discrete logic circuit having logic gates for implementing logic functions upon data signals, an application specific integrated circuit (ASIC) having appropriate combinational logic gates, programmable gate arrays (PGAs), and field programmable gate arrays (FPGAs).

The power adjuster 404 adjusts the amount of power that each of the battery 410, the AC source 412, and the DC source 414 provide to the monitoring device 130 (FIG. 1), or to the defibrillator 212 (FIG. 2). For example, an ambulance generally uses the DC source 414 to provide power to the monitoring device 130 (FIG. 1), or to the defibrillator 212 (FIG. 2). The power adjuster 404 of the ambulance, therefore, connects only the DC source 414 to the local interface 116. Alternatively, for instance, the power adjuster 404 can provide 60% of the power that the defibrillator 212 (FIG. 2) requires to operate, from the DC source 414, and the remaining 40% from the battery 410. The power adjuster 404 can, alternatively, provide 50% of the power that the DC source 414 produces, to the defibrillator 212 (FIG. 2), and the remaining 50% to charge the battery 410. Any power adjuster, battery, and AC and DC source, can be used.

Figure 5:
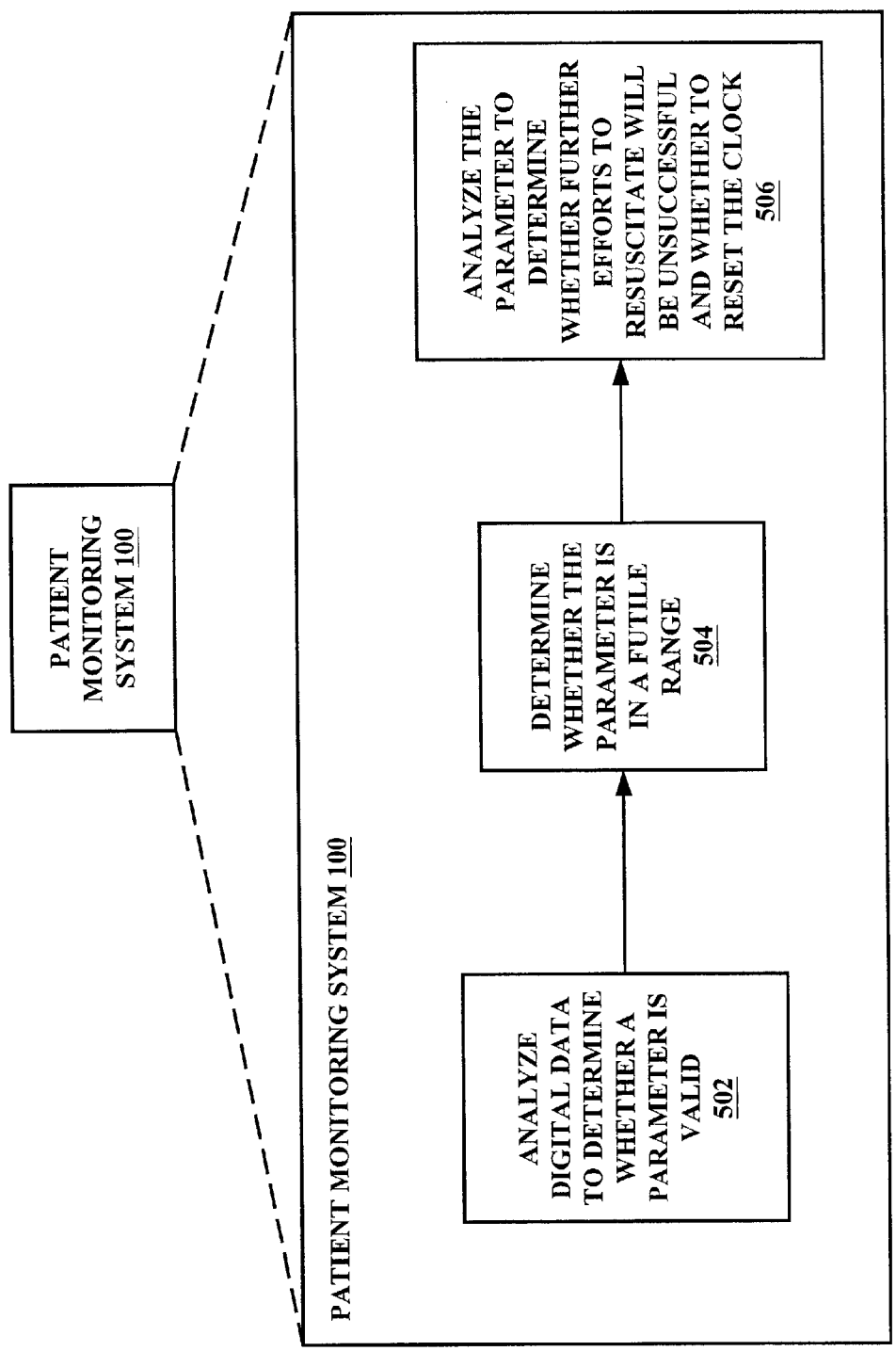
FIG. 5 is a block diagram of an embodiment of the patient monitoring system of FIGS. 1 and 2.

FIG. 5 is a block diagram of an embodiment of the patient monitoring system 100 (FIGS. 1 and 2). The patient monitoring system 100 includes memory modules 502, 504, and 506. The memory modules 502, 504 and 506 store a computer program. The memory module 502 stores a part of the program that analyzes digital data that corresponds to one of the various parameters, to determine whether the parameter is valid.

Whether the parameter is valid depends on various factors. A first factor is whether the sensors 102 (FIGS. 1 and 2) are attached to the patient. If the sensors 102 (FIGS. 1 and 2) are not attached to the patient, the parameter is invalid since there is no connection between the sensors 102 (FIGS. 1 and 2) and the patient. Alternatively, if the sensors 102 (FIGS. 1 and 2) are attached, the parameter may be valid since there is a connection between the sensors 102 (FIGS. 1 and 2) and the patient. A second factor is whether there is a misconnection between the sensors 102 (FIGS. 1 and 2) and the patient. For example, only one of two sensors may be connected to the patient, thereby resulting in a misconnection, and therefore, in an invalid parameter. A third factor is whether the monitoring device 130 (FIG. 1) or the defibrillator 212 (FIG. 2) is faulty because of improperly functioning, old, or improperly maintained parts. A fourth factor is whether the patient is able to keep his/her body part to which the sensors 102 (FIGS. 1 and 2) are attached, stable for a specified amount of time. In such a case, the invalid parameter will be an aberrant, erratic parameter that fluctuates over a very large range, or changes more quickly than the physiology of the patient can cause. For example, if the patient is vigorously shaking his finger, to which the sensors 102 (FIGS. 1 and 2) are attached, vigorously for more than 12 seconds, percent oxygen saturation is invalid since there is an unstable connection between the patient and the sensors 102 (FIGS. 1 and 2) for 12 seconds. A fifth factor is whether there is electrical noise in the environment surrounding the patient. Electrical devices in the environment interfere with measuring one of the various parameters since electromagnetic fields that the electrical devices create can interfere with the signal output by the sensors 102 (FIGS. 1 and 2). Examples of such electrical devices include an electro-surgical knife, and a muscle artifact.

The memory module 504 includes a part of the program that determines whether the valid parameter suggests that further efforts to resuscitate may be unsuccessful. A range in which the valid parameter suggests that further efforts to resuscitate may be unsuccessful, is referred to as a futile range. The futile range can be selected based on studies, or based on customized standards. The studies not only include industry standards, but also published works, for instance, published notes that are based on observations of the patient by doctors. Based on the studies, $EtCO_2$ levels less than 10 mm Hg, CPP from 0 mm Hg to less than 15 mm Hg, central venous oxygen saturation from 0% to less than 30%, CVP less than 30 mm Hg, asystole, and agonal rhythm are considered to be in the futile range. CVP less than 30 mm Hg is considered to be in the futile range since the patient with a CVP less than 30 mm Hg has a 0% chance of return of spontaneous circulation (ROSC). The customized standards are standards that the rescuer arbitrarily selects. For instance, the rescuer can select $EtCO_2$ levels equal to or less than 5 mm Hg to be in the futile range instead of less than 10 mm Hg.

The memory module 506 includes a part of the program that analyzes the parameter to determine whether further efforts to resuscitate will be unsuccessful and whether to reset the clock 132 (FIGS. 1 and 2). Typically, further efforts to resuscitate will be unsuccessful when there is a low chance of ROSC. The analysis can be done based on studies or based on the customized standards. For instance, according to the studies, if the $EtCO_2$ level remains less than 10 mm Hg for 20 minutes, or alternatively, if the central venous oxygen saturation remains less than 30% for any amount of time, there is a low chance of ROSC, thereby determining that further efforts to resuscitate will be unsuccessful and resetting the clock 132 (FIGS. 1 and 2). Furthermore, alternatively, if the patient has agonal rhythm for 25 minutes or more, there is a determination that further efforts to resuscitate will be unsuccessful, and the clock 132 (FIGS. 1 and 2) is reset. Moreover, alternatively, if the patient has asystole for 25 minutes or more, there is a determination that further efforts to resuscitate will be unsuccessful, and the clock 132 (FIGS. 1 and 2) is reset.

The following references are suggested to provide the above-mentioned studies. Krome, Ruiz, Tintinalli, *A Comprehensive Guide,* Emergency Medice, McGraw Hill (4th edition); Bonnin M. J., Pepe, Kimbal K. T., Clark P. S. Jr., *District Criteria For Termination of Resuscitation in the Out of Hospital Setting,* JAMA 270:1457 (1993); Kellerman A. L., Hakcman B. B., Somes G., *Predicting Outcome of Unsuccessful Prehospital Advanced Cardiac Life Support,* JAMA 270:1433 (1993); Levine R. L., Wayne M. A., Miller C. C., *End-Tidal Carbon Dioxide and Outcome of Out-of-Hospital Cardiac Arrest,* NEJM 337:301-6 (1997); Sanders A. B., Kern K. B., Otto C. W. et al, *End-Tidal Carbon Dioxide Monitoring During Cardiopulmonary Resuscitation: A Prognostic Indicator For Survival*, JAMA 262:1347 (1989); Rivers E. P., Martin G. B., Smithline H. et al, *The Clinical Implications of Continuous Central Venous oxygen Saturation during Human CPR.* Ann Emerg. Med. 21:1094 (1992); Paradis N. A., Martin G. B., Rivers E. P. et al, *Coronary Perfusion Pressure and The Return of Spontaneous Circulation in Human Cardiopulmonary Resuscitation,* JAMA 263:1106 (1990); and Nieman J. T., Criley J. M., Rosborough J. P. et al, *Predictive Indicies of Successful Cardiac Resuscitation After Prolonged Arrest and Experimental Cardiopulmonary Resuscitation,* Ann Emerg Med 14:521 (1985). The various parameters mentioned in the studies may vary from patient to patient.

The clock 132 (FIGS. 1 and 2) measures the amount of time for which the various parameters remains within the futile range. For example, the clock 132 (FIGS. 1 and 2) measures whether the patient has agonal rhythm for 25 minutes from the time the I/O devices 120 (FIGS. 1–3) indicate that the patient has an agonal rhythm. As another example, the clock 132 (FIGS. 1 and 2) measures whether the patient has asystole for 25 minutes from the time the I/O devices 120 (FIGS. 1–3) indicate that the patient has asystole.

Figure 6:
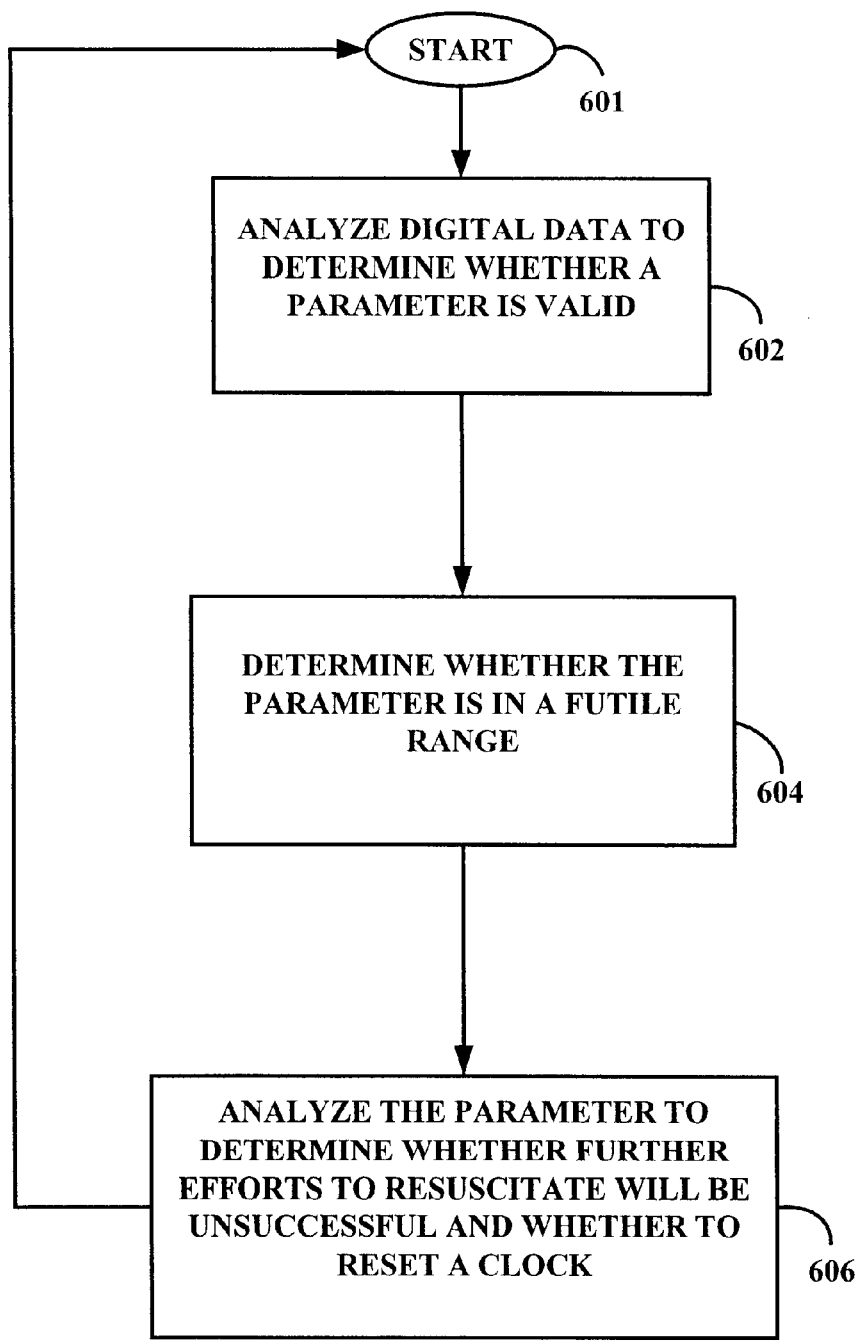
FIG. 6 is a flowchart of an embodiment of a method for determining whether further efforts to resuscitate will be unsuccessful.

FIG. 6 is a flowchart of an embodiment of a method for determining whether further efforts to resuscitate will be unsuccessful. The method starts in step 601. The processor 106 (FIGS. 1 and 2), in step 602, analyzes digital data that corresponds to one of the various parameters that the sensors 102 (FIGS. 1 and 2) measure, to determine whether the parameter is valid.

In step 604, the processor 106 (FIGS. 1 and 2) determines whether the parameter is in the futile range. In step 606, the processor 106 (FIGS. 1 and 2) analyzes the parameter to determine whether to indicate via the I/O devices 120 (FIGS. 1 and 2) that further efforts to resuscitate will be unsuccessful and whether to reset the clock 132 (FIGS. 1, 2). The method then repeats.

Figure 7A:
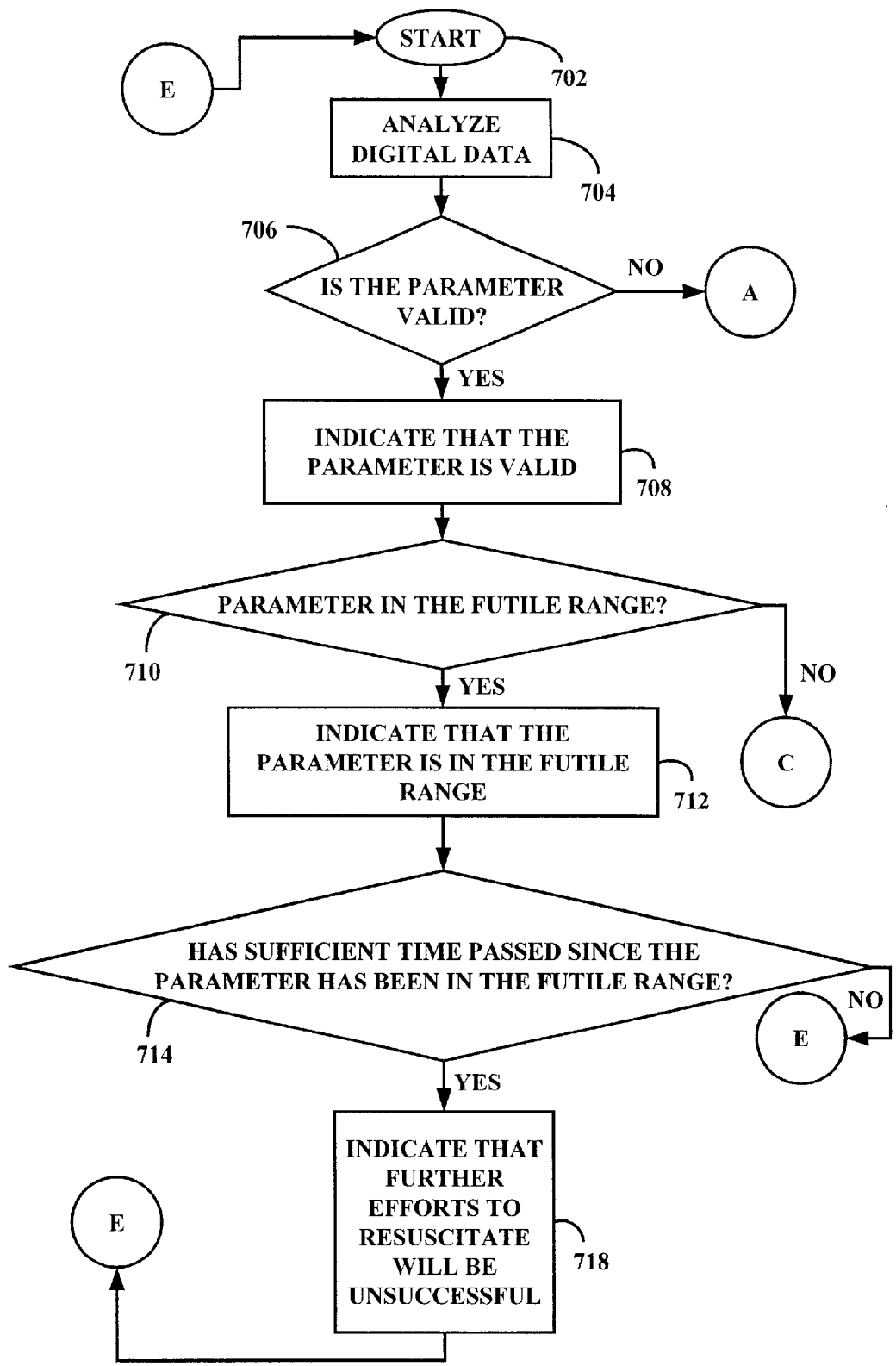
FIGS. 7A–7C are flowcharts of a preferred embodiment of the method.
Figure 7B:
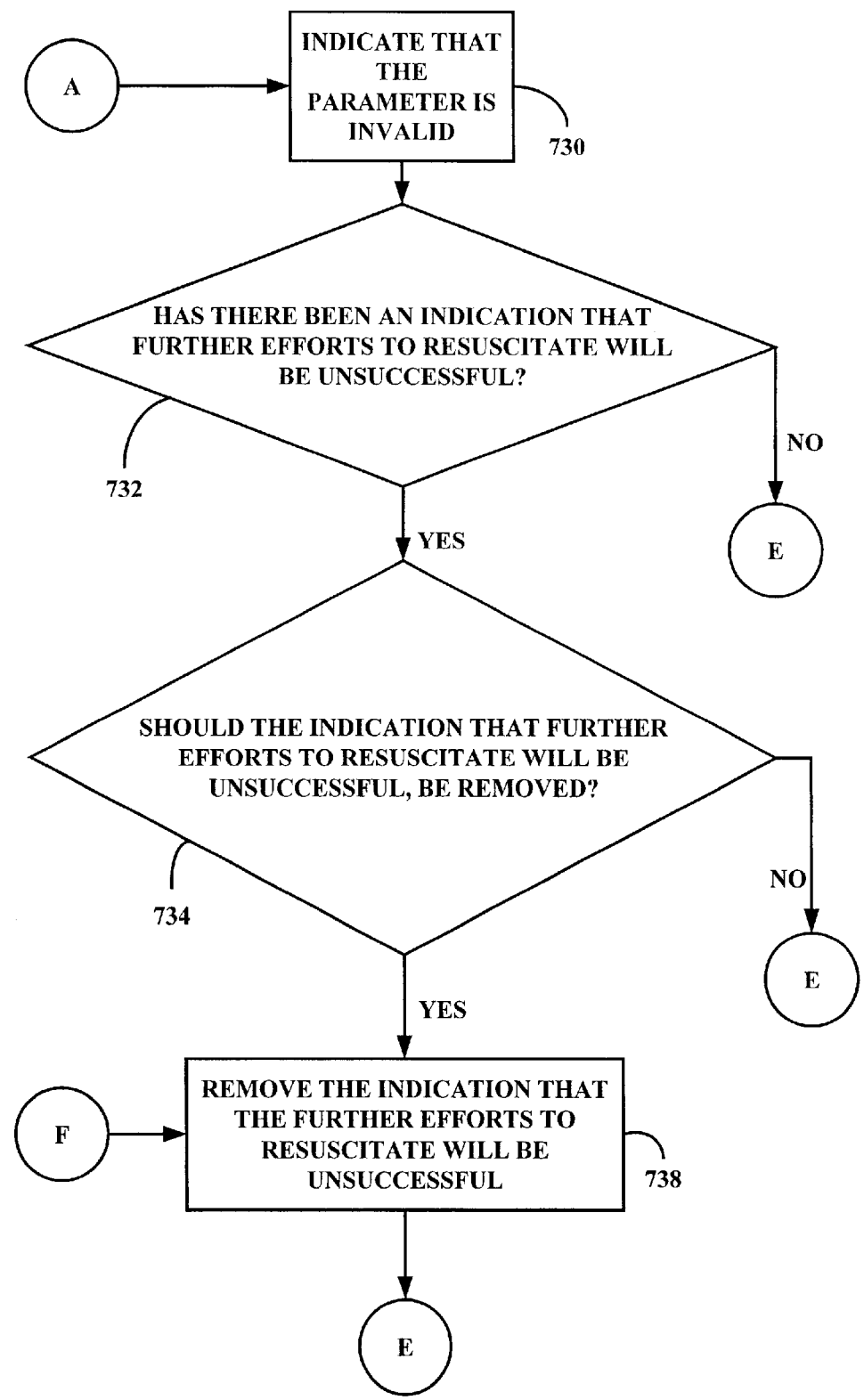
Figure 7C:
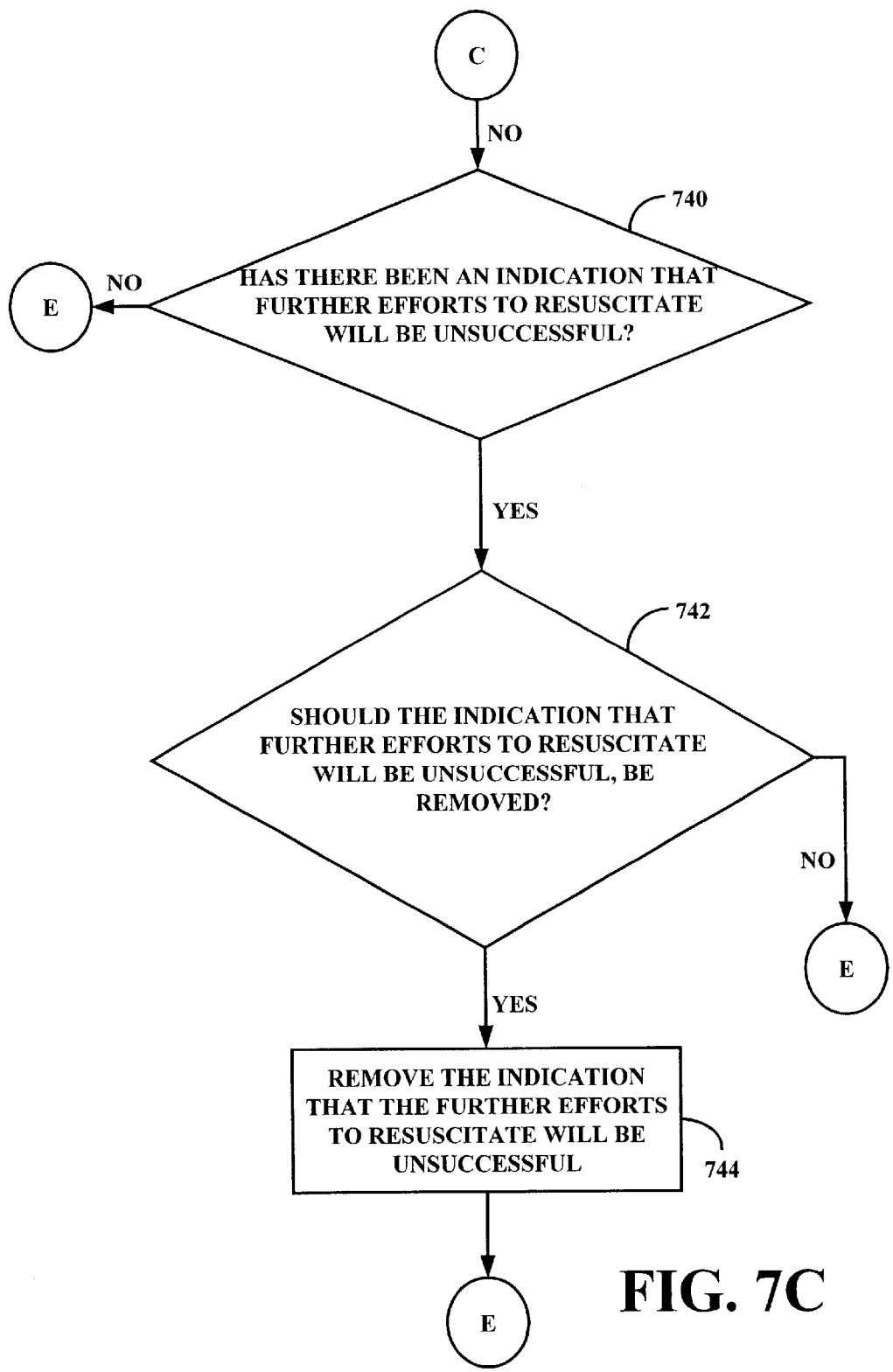

FIGS. 7A–7C are flowcharts of a preferred embodiment of the method. The method starts in a step 702. Step 704 analyzes digital data that corresponds to one of the various parameters. Step 706 determines whether the parameter is valid. If the parameter is valid, according to step 708, the I/O devices 120 (FIGS. 1–3) indicate that the parameter is valid and indicate the parameter. For instance, if the $EtCO_2$ level is 13 mm Hg, the display 302 (FIG. 3) shows that the $EtCO_2$ level is in the valid range, and displays the $EtCO_2$ level of 13 mm Hg.

Step 710 determines whether the parameter is within the futile range. If the parameter is in the futile range, according to step 712, the I/O devices 120 (FIGS. 1–3) indicate that the parameter is in the futile range, and indicate the parameter. For instance, if the CPP is 14 mm Hg, the display 302 (FIG. 3) shows that the CPP is in the futile range and that the CPP is 14 mm Hg.

Step 714 measures the amount of time for which the I/O devices 120 (FIGS. 1–3) indicate that the parameter is in the futile range. The step also measures whether sufficient time has passed to indicate that further efforts to resuscitate will be unsuccessful. The amount of time can be based on the studies or the customized standards. For instance, according to the studies, 25 minutes is a sufficient amount of time for which the I/O devices 120 (FIGS. 1–3) indicate asystole or agonal rhythm.

If sufficient amount of time has passed, the I/O devices 120 (FIGS. 1–3), in the step 718, indicate that further efforts to resuscitate will be unsuccessful, and indicate the amount of time for which the parameter has been in the futile range. Moreover, the clock 132 (FIGS. 1 and 2) is reset and the method starts again with the step 702. For example, if 25 minutes have passed after the I/O devices 120 (FIGS. 1–3) indicate asystole, the display 302 (FIG. 3) shows that further efforts to resuscitate will be unsuccessful, and that the patient had asystole for 25 minutes. Moreover, the clock 132 (FIGS. 1 and 2) is reset.

If sufficient amount of time has not passed, the method repeats itself. During the repetition, if the parameter is still within the futile range, step 714 analyzes whether a sufficient amount of time has passed since the parameter has been in the futile range. Step 714 analyzes after cumulating the amount of time during the initial execution of the method and during the repetition of the method. In other words, step 714 adds the amount of time for which the parameter has been within the futile range during the initial execution and the repetition of the method, and then performs the analysis.

An alternative embodiment of the method may not include step 714 since for some of the various parameters, any amount of time may be sufficient to indicate that further efforts to resuscitate will be unsuccessful and to reset the clock 132 (FIGS. 1 and 2). For instance, if the central venous oxygen saturation is less than 30% for any amount of time, there is a 0% chance of ROSC, and therefore, the I/O devices 120 (FIGS. 1–3) indicate that further efforts to resuscitate will be unsuccessful and the clock 132 (FIGS. 1 and 2) is reset.

In another alternative embodiment of the method, if at least one of the various parameters are valid, and if sufficient amount of time has passed for which the at least one of the various parameters has been in the futile range, the I/O devices 120 (FIGS. 1–3) indicate that further efforts to resuscitate will be unsuccessful and the clock 132 (FIGS. 1 and 2) is reset. The I/O devices 120 (FIGS. 1–3) also indicate the amount of time for which the at least one of the various parameters are in the futile range. For example, if the $EtCO_2$ level is less than 10 mm Hg for 20 minutes, and there is agonal rhythm for at least 25 minutes, sufficient amount of time has passed for each of the two parameters. The display 302 (FIG. 3) shows that further efforts to resuscitate will be unsuccessful, the $EtCO_2$ level of less than 10 mm Hg, the amount of time for which the $EtCO_2$ level remains at less than 10 mm Hg, that there is agonal rhythm, and the amount of time, which is 25 minutes, for which there is agonal rhythm. Moreover, the clock 132 (FIGS. 1 and 2) is reset.

If in step 706, it is determined that the parameter is invalid, in step 730 of FIG. 7B, the I/O devices 120 (FIGS. 1–3) indicate that the parameter is invalid and indicate a sign, such as "?," or "- -" denoting the invalid parameter. For example, when measuring the $EtCO_2$ level of the patient, if the sensors 102 (FIGS. 1 and 2) are unattached to the patient, the I/O devices 120 (FIGS. 1–3) indicate "$EtCO_2$ unplugged" or "$EtCO_2$ failure," to indicate that the parameter is invalid, and indicate a "?".

Once the I/O devices 120 (FIGS. 1–3) indicate that the parameter is invalid, step 732 analyzes whether there has been an indication that further efforts to resuscitate will be unsuccessful. If there has been no such indication, the method starts again with step 702 (FIG. 7A). If there has been such an indication, step 734 analyzes whether the indication that further efforts to resuscitate will be unsuccessful should be removed. In step 738, the indication that further efforts to resuscitate will be unsuccessful, is removed as explained in the following five embodiments.

In one embodiment of the method, the I/O devices 120 (FIGS. 1–3) stop indicating that further efforts to resuscitate will be unsuccessful if the I/O devices indicate twice consecutively that one of the various parameters is invalid. To explain, suppose the method starts again with the step 702 (FIG. 7A) immediately after there is an indication that one of the various parameters is invalid. Once the method starts again, if the I/O devices 120 (FIGS. 1–3) indicate again that the parameter is invalid and if there has been an indication that further efforts to resuscitate will be unsuccessful, the I/O devices 120 (FIGS. 1–3) remove the indication. The parameter during the repetition of the method is the same parameter that was measured during the initial execution of the method. Otherwise, the indication that further efforts to resuscitate will be unsuccessful is not removed, and the method starts again with the step 702 (FIG. 7A). For example, after analyzing digital data that corresponds to an $EtCO_2$ level of the patient, the display 302 (FIG. 3) shows that the $EtCO_2$ level is invalid. The method then starts again with the step 702 (FIG. 7A), and analyzes digital data that corresponds to an $EtCO_2$ level of the patient. If the $EtCO_2$ level is invalid for a second time, the indication that further efforts to resuscitate will be unsuccessful is removed. Otherwise, the indication that further efforts to resuscitate will be unsuccessful is not removed and the method starts again with the step 702 (FIG. 7A).

Similarly, in a second embodiment of the method, the indication that further efforts to resuscitate will be unsuccessful is removed, in step 738, after the I/O devices 120 (FIGS. 1–3) indicate that one of the various parameters is invalid for any number of repetitions of the method. Otherwise, the indication that further efforts to resuscitate will be unsuccessful, is not removed, and the method starts again with the step 702 (FIG. 7A). For each of the multiple repetitions of the method, digital data that corresponds to the same parameter, is analyzed.

In a third embodiment of the method, the indication that further efforts to resuscitate will be unsuccessful, is removed, in the step 738, if a sufficient amount of time has passed after the I/O devices 120 (FIGS. 1–3) indicate that one of the various parameters is invalid and if there has been an indication that further efforts to resuscitate will be unsuccessful. Otherwise, the indication that further efforts to resuscitate will be unsuccessful, is not removed.

In a fourth embodiment of the method, the indication that further efforts to resuscitate will be unsuccessful, is removed in step 738, if after an indication that one the various parameters is invalid, the method goes directly to the step 702 (FIG. 7A) and there is an indication that another one of the various parameters is invalid. Otherwise, the indication that further efforts to resuscitate will be unsuccessful, is not removed, and the method starts again with the step 702 (FIG. 7A). The indication that further efforts to resuscitate will be unsuccessful is removed after there has been such an indication. When the method repeats by going back directly to the step 702 (FIG. 7A), the method uses digital data that corresponds to one of the various parameters that has not been analyzed during the prior execution of the method. For example, if after analyzing digital data that corresponds to an $EtCO_2$ level of the patient, the display 302 (FIG. 3) shows that the $EtCO_2$ level is invalid, the method starts again with the step 702 (FIG. 7A), and analyzes digital data that corresponds to a CPP of the patient. If the CPP is invalid and if there has been an indication that further efforts to resuscitate will be unsuccessful, the indication that further efforts to resuscitate will be unsuccessful, is removed. Otherwise, the indication that further efforts to resuscitate will be unsuccessful is not removed, and the method starts with the step 702 (FIG. 7A).

Similarly, in a fifth embodiment of the method, the indication that further efforts to resuscitate will be unsuccessful is removed in step 738, if after analyzing digital data that correspond to some of the various parameters, the I/O devices 120 (FIGS. 1–3) indicate that at least one of some of the various parameters are invalid. Otherwise, the indication that further efforts to resuscitate will be unsuccessful, is not removed, and the method returns starts again with the step 702 (FIG. 7A). The method repeats itself after the step 738, and analyzes digital data that corresponds to one of the various parameters.

If in step 710 (FIG. 7A), it is determined that one of the various parameters is outside the futile range, the method analyzes, in step 740 of FIG. 7C, whether there has been an indication that further efforts to resuscitate will be unsuccessful. If there has been no such indication, the method starts again from the step 702 (FIG. 7A). If there has been such an indication, step 742 analyzes whether the indication that further efforts to resuscitate will be unsuccessful should be removed. In step 744, the indication that further efforts to resuscitate will be unsuccessful is removed as explained in the following five embodiments.

In a sixth embodiment of the method, the I/O devices 120 (FIGS. 1–3) stop indicating that further efforts to resuscitate will be unsuccessful, if the I/O devices indicate twice consecutively that one of the various parameters is outside the futile range. To explain, suppose the method starts again with the step 702 (FIG. 7A) immediately after there is an indication that one of the various parameters is outside the futile range. Once the method starts again, if the I/O devices 120 (FIGS. 1–3) indicate again that the parameter is outside the futile range and if there has been an indication that further efforts to resuscitate will be unsuccessful, the I/O devices 120 (FIGS. 1–3) remove the indication. The parameter during the repetition of the method is the same parameter that was measured during the initial execution of the method. Otherwise, the indication that further efforts to resuscitate will be unsuccessful is not removed, and the method starts again with the step 702 (FIG. 7A). For instance, after analyzing digital data that corresponds to an $EtCO_2$ level of the patient, the display 302 (FIG. 3) shows that the $EtCO_2$ level is outside the futile range. The method then starts again with the step 702 (FIG. 7A), analyzes digital data that corresponds to an $EtCO_2$ level of the patient. If the $EtCO_2$ level is outside the futile range for a second time, the indication that further efforts to resuscitate will be unsuccessful, is removed. Otherwise, the indication that further efforts to resuscitate will be unsuccessful, is not removed, and the method starts again with the step 702 (FIG. 7A).

Similarly, in a seventh embodiment of the method, the indication that further efforts to resuscitate will be unsuccessful is removed, in step 744, after the I/O devices 120 (FIGS. 1–3) indicate that one of the various parameters is outside the futile range for any number of repetitions of the method. Otherwise, the indication that further efforts to resuscitate will be unsuccessful, is not removed, and the method starts again with the step 702 (FIG. 7A). For each of the multiple repetitions of the method, digital data that corresponds to the same parameter, is analyzed.

In an eighth embodiment of the method, the indication that further efforts to resuscitate will be unsuccessful, can be removed, in step 744, if a sufficient amount of time has passed after the I/O devices 120 (FIGS. 1–3) indicate that one of the various parameters is outside the futile range and if there has been an indication that further efforts to resuscitate will be unsuccessful. Otherwise, the indication that further efforts to resuscitate will be unsuccessful, is not removed.

In a ninth embodiment of the method, the indication that further efforts to resuscitate will be unsuccessful is removed in the step 744, if after an indication that one the various parameters is outside the futile range, the method goes directly to the step 702 (FIG. 7A), and there is an indication that another one of the various parameters, is outside the futile range. Otherwise, the indication that further efforts to resuscitate will be unsuccessful is not removed, and the method starts again with the step 702 (FIG. 7A). The indication that further efforts to resuscitate will be unsuccessful is removed after there has been such an indication. When the method repeats by going back directly to the step 702 (FIG. 7A), the method uses digital data that corresponds to one of the various parameters that has not been analyzed during the prior execution of the method. For example, if after analyzing digital data that corresponds to an $EtCO_2$ level of the patient, the display 302 (FIG. 3) shows that the $EtCO_2$ level is outside the futile range, the method starts again with the step 702 (FIG. 7A), and analyzes digital data that corresponds to a CPP of the patient. If the CPP is outside the futile range and if there has been an indication that further efforts to resuscitate will be unsuccessful, the indication that further efforts to resuscitate will be unsuccessful, is removed. Otherwise, the indication that further efforts to resuscitate will be unsuccessful is not removed, and the method starts with the step 702 (FIG. 7A).

Similarly, in a tenth embodiment of the method, the indication that further efforts to resuscitate will be unsuccessful is removed in the step 744, if after analyzing digital data that correspond to some of the various parameters, the I/O devices 120 (FIGS. 1–3) indicate that at least one of some of the various parameters are outside the futile range. Otherwise, the indication that further efforts to resuscitate will be unsuccessful is not removed, and the method returns starts again with the step 702 (FIG. 7A). The method repeats itself after the step 744, and analyzes digital data that corresponds to one of the various parameters.

The patient monitoring system 100 (FIGS. 1, 2 and 5), if implemented in software, or the method of FIGS. 6, and 7A–7C, each of which includes an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device.

The computer-readable medium can be, for example but not limited to, an electronic, magnetic, optical, electromagnetic, infrared, or semiconductor system, apparatus, device, or propagation medium. More specific examples of the computer-readable medium would include an electrical connection having one or more wires, a portable computing device diskette, a RAM, a ROM, an erasable programmable ROM (EPROM), an electrically EPROM (EEPROM), a flash memory, an optical fiber, and a portable CDROM. Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

In an alternative embodiment, where the patient monitoring system 100 (FIGS. 1, 2, and 5) is implemented in hardware, the patient monitoring system 100 (FIGS. 1, 2, and 5) can be implemented with any or a combination of the following technologies: a discrete logic circuit having logic gates for implementing logic functions upon data signals, an ASIC having appropriate combinational logic gates, PGAs, and FPGAs.

The flow charts of FIGS. 6, and 7A–7C show the architecture, functionality, and operation of a possible implementation of the software implementation of the patient monitoring system 100 of FIGS. 1, 2, and 5, respectively. In this regard, each block represents a module, segment, or portion of code, which includes one or more executable instructions for implementing the specified logical function(s). It should also be noted that in some alternative implementations, the functions noted in the blocks may occur out of the order noted in the FIGS. 6, and 7A–7C. For example, two blocks shown in succession in FIG. 7A may in fact be executed substantially concurrently or the blocks may sometimes be executed in the reverse order, depending upon the functionality involved, as will be further clarified below.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A method for determining whether an attempt to resuscitate a patient would be unsuccessful, comprising the steps of:

receiving digital data that is representative of a medical status of the patient and corresponds to a parameter;

analyzing the digital data to determine whether the parameter is valid;

determining whether the parameter is in a first range; and analyzing the parameter, based on the determinations regarding the parameter, to decide whether the attempt to resuscitate the patient would be unsuccessful.

2. The method of claim 1, wherein the step of analyzing the parameter to decide whether the attempt to resuscitate the patient would be unsuccessful, comprises the steps of:

calculating an amount of time for which the parameter is in the first range; and determining whether the parameter is in the first range for a sufficient amount of time, the method further comprising the step of indicating that the attempt to resuscitate the patient would be unsuccessful due to a determination that the parameter is in the first range for a sufficient amount of time.

3. The method of claim 1, further comprising the steps of:

analyzing the parameter if the parameter is determined other than valid, to determine whether to remove an indication that the attempt to resuscitate the patient would be unsuccessful; and if the parameter is determined to be valid, analyzing digital data that respectively corresponds to at least one other parameter to determine respective validity for the at least one other parameter, and, if invalidity is determined for any of the at least one other parameter, analyzing the first parameter that is determined to be invalid, to determine whether to remove an indication that the attempt to resuscitate the patient would be unsuccessful.

4. The method of claim 3, wherein the step of analyzing the first parameter that is determined to be invalid, to determine whether to remove the indication that the attempt to resuscitate the patient would be unsuccessful, comprises the steps of:

measuring a number of times for which the first parameter is determined to be invalid; and determining whether to remove the indication that the attempt to resuscitate the patient would be unsuccessful based on the number of times.

5. The method of claim 3, wherein the step of analyzing the first parameter that is determined to be invalid, to determine whether to remove the indication that the attempt to resuscitate the patient would be unsuccessful, comprises the steps of:

measuring an amount of time for which the first parameter is invalid; and determining whether to remove the indication that the attempt to resuscitate the patient would be unsuccessful based on detection that the amount of time is sufficiently large.

6. The method claim 1, wherein the parameter is a measure of percent oxygen saturation.

7. The method of claim 1, further including the step of, after an unsuccessful attempt to resuscitate said patient has been made, determining whether a further attempt to resuscitate said patient would be unsuccessful.

8. The method of claim 7, wherein said further attempt implements the same technique as the attempt that has already been made.

9. A method for determining whether an attempt to resuscitate a patient would be unsuccessful, comprising the steps of:

receiving digital data that are representative of a medical status of the patient and that correspond to a plurality of parameters analyzing the digital data to determine whether each of the plurality of parameters is valid and is in a respective range; and analyzing, if at least two of the plurality of parameters fall within their respective ranges and are valid, the first and second parameters that fall within their respective ranges, to determine whether the attempt to resuscitate the patient would be unsuccessful.

10. The method of claim 9 wherein the step of analyzing the first and second parameters that fall within their respective ranges, to determine whether the attempt to resuscitate the patient would be unsuccessful, comprises the steps of:

calculating first and second amounts of time for which the first and second parameters are in their respective ranges; and determining whether the first amount of time is a first sufficient amount of time, and the second amount of time is a second sufficient amount of time, the method further comprising the step of indicating, due to a determination that the first amount of time is a first sufficient amount of time, and the second amount of time is a second sufficient amount of time, that the attempt to resuscitate the patient would be unsuccessful.

11. The method of claim 9, further comprising the step of analyzing the first parameter that is determined other than valid, and the second parameter that is determined to be invalid, to determine whether to remove an indication that the attempt to resuscitate the patient would be unsuccessful.

12. The method of claim 11, wherein the step of analyzing the first parameter that is determined to be invalid, and the second parameter that is determined to be invalid, to determine whether to remove the indication that the attempt to resuscitate the patient would be unsuccessful further comprises the step of removing the indication that the attempt to resuscitate the patient would be unsuccessful based on a determination that the first parameter is invalid and the second parameter is invalid.

13. A system for determining whether an attempt to resuscitate a patient would be unsuccessful, comprising:

a processor;

a clock for producing timing information;

a memory readable by the processor; and external to said memory, a source of digital data that are representative of a medical status of the patient and respectively correspond to at least one parameter, said memory including a program that, under execution by the processor,:

receives the digital data;

analyzes the digital data to respectively determine whether the at least one parameter is valid;

determines whether the at least one parameter is in a respective range;

receives the timing information;

calculates, based on the timing information, an amount of time for which a parameter is in its respective range; and determines, based on the calculation and analysis, whether the attempt to resuscitate the patient would be unsuccessful.

14. The system of claim 13, further comprising a device for resuscitate the patient that indicates, due to a determination that a parameter is in its respective range for a sufficient amount of time, that the attempt to resuscitate the patient would be unsuccessful.

15. The system of claim 14, wherein, if a parameter is determined other than valid, the program further analyzes the first parameter that is determined to be invalid, to determine whether to remove the indication that the attempt to resuscitate the patient would be unsuccessful.

16. The system of claim 15, wherein the program comprises:

means for counting a number of times the program determines that the first parameter is invalid; and means for determining to remove the indication that the attempt to resuscitate the patient would be unsuccessful based on the number of times.

17. The system of claim 15, further comprising:

means for measuring an amount of time for which the first parameter is invalid; and means for removing the indication that the attempt to resuscitate the patient would be unsuccessful based on detection that the amount of time is sufficiently large.

18. A system for determining whether an attempt to resuscitate a patient would be unsuccessful, comprising:

a processor;

a clock for producing timing information;

a memory readable by the processor; and external to said memory, a source of digital data that is representative of a medical status of the patient and that respectively correspond to at least one parameter, said memory including a program that, under execution by the processor,:
receives the digital data;
analyzes the digital data to respectively determine whether the at least one parameter is valid;
determines whether the at least one parameter is in a respective range;
receives the timing information;
calculates, based on the timing information, an amount of time for which a first and second of the at least one parameter are in their respective ranges; and
determines, based on the calculation and analysis, whether the attempt to resuscitate the patient would be unsuccessful.

19. The system of claim 18, further comprising a device for indicating that the attempt to resuscitate the patient would be unsuccessful due to a determination that the first and second parameters are in their respective ranges for a first sufficient amount of time and for a second sufficient amount of time, respectively.

20. The system of claim 18, wherein, if at least two parameters are determined other than valid, the program further analyzes the first parameter that is determined to be invalid, and the second parameter that is determined to be invalid, to determine whether to remove an indication that the attempt to resuscitate the patient would be unsuccessful.

21. The system of claim 20, wherein, if at least two parameters are determined to be invalid, the program determines to remove the indication that the attempt to resuscitate the patient would be unsuccessful, based on the analysis of the first and second parameters that are determined to be invalid.

22. A system for determining whether an attempt to resuscitate a patient would be unsuccessful, comprising:
means for analyzing digital data that is representative of a status of the patient and corresponds to a first parameter to determine whether the first parameter is valid;
means for determining whether the first parameter is in a first range; and
means for deciding, based on the determinations regarding the first parameter, whether the attempt to resuscitate the patient would be unsuccessful.

23. A computer-readable medium, the computer-readable medium comprising a computer program for determining whether an attempt to resuscitate a patient would be unsuccessful, the computer program performing the steps of:
inputting digital data that is representative of a status of the patient and corresponds to a first parameter;
determining, based on the digital data, whether the first parameter is valid;
determining whether the first parameter is in a first range; and
deciding, based on the determinations regarding the parameter, whether the attempt to resuscitate the patient would be unsuccessful.

24. A system for determining whether an attempt to resuscitate a patient would be unsuccessful, comprising:
a sensor that measures a parameter of data that is representative of a medical status of the patient and outputs analog data representative of the parameter;
means for converting the analog data to digital data; and
a processor that:
receives the digital data that corresponds to the parameter;
determines, based on the digital data, whether the parameter is valid;
determines whether the parameter is in a predetermined range; and
decides, based on the determinations regarding the parameter, whether the attempt to resuscitate the patient would be unsuccessful.

25. A system for determining whether an attempt to resuscitate a patient would be unsuccessful, comprising:
a sensor that measures first and second parameters of data that are representative of a medical status of the patient and that outputs analog data respectively representative of the measurements;
means for converting the analog data to digital data; and
a processor that:
receives the digital data that corresponds to the first parameter;
determines, based on digital data that corresponds to the first parameter, whether the first parameter is valid;
determines whether the first parameter is in a first range;
receives digital data that corresponds to a second parameter;
determines, based on the digital data that corresponds to the second parameter, whether the second parameter is valid;
determines whether the second parameter is in a second range; and
determines, if the first and second parameters fall in the first and second ranges and are valid respectively, whether the attempt to resuscitate the patient would be unsuccessful.

* * * * *